US007777080B2

(12) United States Patent
Wolter et al.

(10) Patent No.: US 7,777,080 B2
(45) Date of Patent: Aug. 17, 2010

(54) CARBOXYLIC ACID DERIVATIVES CONTAINING PHOSPHOROUS GROUPS AND ORGANICALLY POLYMERIZABLE GROUPS

(75) Inventors: Herbert Wolter, Tauberbischofsheim (DE); Somchith Nique, Schorndorf (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 601 days.

(21) Appl. No.: 10/527,326

(22) PCT Filed: Sep. 11, 2003

(86) PCT No.: PCT/EP03/10131

§ 371 (c)(1),
(2), (4) Date: Oct. 31, 2005

(87) PCT Pub. No.: WO2004/026884

PCT Pub. Date: Apr. 1, 2004

(65) Prior Publication Data

US 2006/0142515 A1 Jun. 29, 2006

(30) Foreign Application Priority Data

Sep. 11, 2002 (DE) ................. 102 42 106

(51) Int. Cl.
C07F 9/02 (2006.01)
C08F 30/02 (2006.01)
C08F 130/02 (2006.01)
C08F 230/02 (2006.01)
C08G 79/02 (2006.01)

(52) U.S. Cl. ................. 568/14; 568/8; 568/15; 526/274; 526/278; 528/167; 528/168

(58) Field of Classification Search ................. 526/274, 526/278; 568/14, 8, 15; 528/167, 168
See application file for complete search history.

(56) References Cited

U.S. PATENT DOCUMENTS

| 2,273,891 | A | * | 2/1942 | Pollack et al. ................. 526/71 |
| 2,409,633 | A | * | 10/1946 | Kropa ................. 525/44 |
| 2,934,554 | A | * | 4/1960 | Lane ................. 558/85 |
| 3,078,256 | A | * | 2/1963 | Wittig et al. ................. 554/153 |
| 3,299,015 | A | * | 1/1967 | Miller ................. 526/278 |
| 3,351,617 | A | * | 11/1967 | Jaeger et al. ................. 526/278 |
| 3,361,784 | A | * | 1/1968 | Leu ................. 524/131 |
| 3,426,004 | A | * | 2/1969 | Wagner ................. 526/274 |
| 3,437,719 | A | * | 4/1969 | Sullivan et al. ................. 525/209 |
| 3,762,865 | A | | 10/1973 | Keine |
| 3,839,207 | A | | 10/1974 | Keine |
| 4,044,075 | A | | 8/1977 | Jaeger |
| 4,066,597 | A | * | 1/1978 | Jager ................. 524/98 |
| 4,104,309 | A | * | 8/1978 | Sleziona et al. ................. 568/14 |
| 4,222,780 | A | | 9/1980 | Shibatani et al. |
| 4,259,117 | A | | 3/1981 | Yamauchi et al. |
| 4,499,251 | A | * | 2/1985 | Omura et al. ................. 526/278 |
| 4,514,342 | A | * | 4/1985 | Billington et al. ................. 558/180 |
| 4,581,180 | A | * | 4/1986 | Yokoshima et al. ................. 558/180 |
| 4,612,384 | A | * | 9/1986 | Omura et al. ................. 558/198 |
| 4,954,399 | A | * | 9/1990 | Tani et al. ................. 428/402 |
| 5,444,123 | A | * | 8/1995 | Zeltner et al. ................. 525/133 |
| 5,804,680 | A | * | 9/1998 | Plundrich et al. ................. 526/274 |
| 6,124,491 | A | | 9/2000 | Wolter et al. |
| 6,172,131 | B1 | | 1/2001 | Moszner et al. |
| 6,242,433 | B1 | | 6/2001 | Balsamo et al. |
| 6,245,872 | B1 | * | 6/2001 | Frey et al. ................. 526/277 |
| 6,339,114 | B1 | * | 1/2002 | Klee et al. ................. 523/116 |
| 6,433,117 | B1 | * | 8/2002 | Ma et al. ................. 526/277 |
| 6,458,868 | B1 | * | 10/2002 | Okada et al. ................. 523/116 |
| 6,566,474 | B1 | * | 5/2003 | O'Lenick, Jr. ................. 526/277 |
| 6,617,409 | B2 | * | 9/2003 | Yukawa et al. ................. 526/277 |
| 6,835,790 | B2 | * | 12/2004 | Fukuhara et al. ................. 526/333 |
| 6,900,251 | B2 | * | 5/2005 | Moszner et al. ................. 522/171 |
| 6,902,608 | B2 | * | 6/2005 | Erdmann et al. ................. 106/35 |
| 7,041,714 | B2 | * | 5/2006 | Takeshita et al. ................. 523/118 |
| 7,160,968 | B2 | * | 1/2007 | Ito et al. ................. 526/277 |
| 2002/0068802 | A1 | * | 6/2002 | Mueller et al. ................. 526/274 |
| 2002/0107298 | A1 | * | 8/2002 | Al-Akhdar et al. ................. 522/7 |
| 2003/0036582 | A1 | * | 2/2003 | Yamakawa et al. ................. 523/115 |
| 2003/0055123 | A1 | * | 3/2003 | Kawashima et al. ................. 523/116 |
| 2003/0167968 | A1 | * | 9/2003 | Erdmann et al. ................. 106/35 |
| 2003/0186197 | A1 | * | 10/2003 | Allred et al. ................. 433/226 |
| 2004/0034182 | A1 | * | 2/2004 | Raether et al. ................. 526/274 |
| 2004/0167288 | A1 | * | 8/2004 | Taylor ................. 525/221 |
| 2005/0014861 | A1 | * | 1/2005 | Qian ................. 523/116 |

FOREIGN PATENT DOCUMENTS

DE 14 95 383 A 4/1969

(Continued)

OTHER PUBLICATIONS

Hatakeyama et al., A synthesis of (-)-pyrenophorin using a 4-(dimethylamino)pyridine catalyzed ester exchange reaction of phosphonoacetates wtih lactols, 1987, Tetrahedron Letters, 28(24), pp. 2717-2720.*

(Continued)

Primary Examiner—Mark Eashoo
Assistant Examiner—Liam J Heincer
(74) Attorney, Agent, or Firm—Stephen A. Bent; Foley & Lardner LLP

(57) ABSTRACT

The invention relates to carboxylic acid derivates which contain at least one organically polymerisable group and at least one group which contains phosphorous and is reactive or that modulates the properties of the molecule. The invention also relates to a method for production of the inventive molecules and the use thereof in dentistry and for influencing the properties of materials.

23 Claims, No Drawings

FOREIGN PATENT DOCUMENTS

| | | | |
|---|---|---|---|
| DE | 27 11 234 A1 | 3/1977 |
| DE | 44 16 857 C1 | 5/1994 |
| DE | 196 46 708 A1 | 10/1997 |
| DE | 199 18 974 A1 | 4/1999 |
| EP | 0 667 364 A | 8/1995 |
| EP | 0554 890 A1 | 8/1996 |
| FR | 1 395 178 | 4/1964 |
| FR | 2 767 829 A | 3/1999 |
| JP | 9-124668 | 5/1997 |
| WO | WO 00/58316 | 10/2000 |
| WO | WO 0058316 A1 * | 10/2000 |
| WO | WO 01 74826 A1 | 10/2001 |
| WO | WO 0202057 A1 * | 1/2002 |
| WO | WO 02 088222 A1 | 11/2002 |

OTHER PUBLICATIONS

International Search Report of PCT/EP03/10131.

Database CA Online!, Chemical Abstracts Service, Columbus, Ohio, US, Eiichi Kato, "Oil-based inks for electrostatic ink-jet printing producing images with good clarity and high strength and freedom from nozzle clogging", retrieved from STN Database accession No. 138:370460 XP002266660 Verbindung 28 Zusammenfassung & JP 2003 138183 A (Fuji Photo Film Co., Ltd. Japan) May 14, 2003.

Database Crossfire Beilstein Online! Beilstein Institut zur Förderung der Chemischen Wissenschaften, Frankfurt am Main, DE; Database accession No. BRN 7176797; BRN 7175561 XP002266661 Zusammenfassung & Hewitt, D. G. et al.; Aust. J. Chem. Nr. 37, 1984, Seiten 1631-1642.

* cited by examiner

CARBOXYLIC ACID DERIVATIVES CONTAINING PHOSPHOROUS GROUPS AND ORGANICALLY POLYMERIZABLE GROUPS

The present invention relates to new carboxylic acid derivatives which exhibit at least one organically polymerizable group and at least one phosphorus-comprising group which is reactive or which adjusts the properties of the molecule. In addition, the invention relates to processes for the preparation of the molecules according to the invention and to their use in the dental field and for influencing the properties of materials.

Numerous organically substituted phosphorus compounds, optionally also comprising C=C double bonds, are known which can be incorporated in organic polymers or directly polymerized. The presence of phosphorus-comprising groups in polymers can have a positive effect on a number of properties of these compounds, e.g. can bring about an increase in the thermal stability, a decrease in the flammability, an improvement in the adhesive properties and/or an improvement in the solubility in polar solvents. Phosphorus compounds comprising a double bond (e.g. appropriately substituted phosphonic acid derivatives) are in particular also used in the dental field, where they represent, e.g. because of the complexing of $Ca^{2+}$ ions, very effective bonding agents.

There are admittedly disadvantages to the known polymerizable phosphorus compounds. Thus, those compounds in which the phosphorus atom(s) is/are bonded via oxygen to the organic component of the molecule are hydrolytically unstable. For example, DE 27 11 234 C3 of Kuraray Co. reveals phosphoric acid diesters, both ester groups of which are each saponified in aqueous medium, and phosphonic acid esters, which still exhibit a hydrolyzable group. EP 0 554 890 of Dentspley reveals poly(meth)acrylates derivatized with phosphoric acid as basis for light-curable glass ionomer cements which are likewise sensitive to hydrolysis. However, materials suitable for the dental field ought not to have this property since they, in the mouth, are continually exposed to an environment with a high moisture content. Admittedly, there are also a number of phosphorus compounds comprising a double bond in which the or an organic group is bonded directly to the phosphorus. However, these can only be prepared at very great cost. Thus, DE 199 18 974 A1 discloses dental materials with polymerizable phosphonic acids which are highly suitable as dental filling materials since they guarantee strong and lasting bonding of the filling material to the tooth base. These dental materials are (meth)acrylic acid-phosphonic acid alkyl esters which are accessible in the following way: phosphoric acid dialkyl esters are reacted with ethers comprising double bonds to give monoalkylphosphonic acid esters which, optionally after hydrolysis, are reacted with (meth)acryloyl chloride. The product is subsequently subjected to hydrolysis. The preparation of the hydrolysis-stable and polymerizable acrylophosphonic acid of DE 197 46 708 C2 requires the synthesis of halomethylacrylic acid esters and of protected mono- or difunctional phosphonic acid esters and thus of starting compounds which in each case can only be prepared with great difficulty and expense.

It is an object of the present invention to make available organically polymerizable phosphorus-comprising compounds which, on the one hand, are stable to hydrolysis within the meaning given above and, on the other hand, are relatively simple to access. In particular, but not only, these compounds should be suitable for the preparation of materials which can be used in the dental field.

Surprisingly, it could be found that carboxylic acid derivatives with at least one phosphorus-comprising group connected to the carbon of the acid part of the molecules and at least one organically polymerizable group in the acid derivative part of the molecule (i.e. in the ester, amide or thioester residue or the like) solve the problem posed.

According to the invention, compounds of the formula

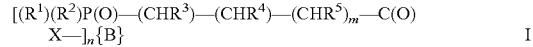

are therefore prepared in which the residues and indices have the following meanings:

X is O, NH, $NR^6$ or S, $R^1$ and $R^2$ can, independently of one another, be hydrogen; preferably they are optionally substituted alkyl, alkenyl, aryl, alkylaryl or arylalkyl or optionally substituted alkoxy, alkenyloxy, aryloxy, alkylaryloxy or arylalkyloxy with very preferably 1-6 carbon atoms in each case for open-chain aliphatic groups and very preferably 6 to 12 carbon atoms for cycloaliphatic or aromatic groups, in which the substitution can be carried out, for example, with halogen or amino groups or oxygen-comprising and/or sulfur-comprising residues, $R^3$, $R^4$, $R^5$ and $R^6$ are, independently of one another, hydrogen or optionally substituted alkyl, alkenyl, aryl, alkylaryl or arylalkyl with preferably 1-6 carbon atoms in each case for open-chain aliphatic groups and preferably 6 to 12 carbon atoms for cycloaliphatic or aromatic groups, in which the substitution can be carried out, for example, with halogen or amino groups or oxygen-comprising and/or sulfur-comprising residues, {B} is a straight-chain or branched residue with at least one organically polymerizable group, in which a C=C double bond is preferably concerned, and at least 2, better still 3 and preferably 4 and likewise preferably up to 50 carbon atoms;

{B} exhibits n bonds to the n phosphorus-comprising residues, the definition of which is put in square brackets;

m is preferably 0 but can also be 1, 2, 3, 4 or optionally even a higher number, and n is preferably 1 but can also be 2, 3, 4 or optionally even a higher number.

The following are to be excluded from the scope of protection: [4-oxo-4-(2-propenylamino)butyl]phenylphosphinic acid ethyl ester, [4-oxo-4-(2-propenylamino)butyl]phosphonic acid diethyl ester; compounds of the formula $(RO)_2P(O)CH_2CHR^1CONHCH_2NHCOCR^2=CR^3R^4$ with R=methyl or butyl, $R^1$=H or methyl, $R^2$=H, $CH_2CO_2H$ or methyl, $R^3$=H and $R^4$=H, methyl, $CONH_2$ or $CO_2H$;

$CH_2=C(R^1)C(O)O(CH_2)_xO(CO)CH(R^2)CH_2—P(O)R^4(OR^3)$ and $CH_2=C(R^1)CH_2O(CO)CH(R^2)CH_2—P(O)R^4(OR^3)$ with $R^1$ and $R^2$=hydrogen or methyl, $R^3$=$C_1$-$C_{18}$-alkyl, benzyl or phenyl, $R^4$ is hydrogen or a $C_1$-$C_4$-alkyl and x is 1 to 30, in particular 2-4, and in particular 3-[hydroxy(phenyl)phosphinyl]propionic acid(2-methacryloyloxyethyl)ester. These compounds are already known in the state of the art.

{B} is, as mentioned, a residue with n bonds to the n phosphorus-comprising residues. If n is greater than 1, {B} correspondingly comprises several groups which are bonded via X to these residues. The organically polymerizable group(s) of the residue {B} can essentially be chosen in any way. In this connection, they are preferably vinyl, allyl, norbornene, glycidyl, acrylate or methacrylate groups, thioacrylate or thiomethacrylate groups or groups derived from other (meth)acrylic acid derivatives, such as from the acid amides.

The vinyl or allyl groups are in this connection expediently linked via a pure carbon chain to the group C(O)X which connects the phosphorus part of the molecule to the part {B}. Particularly preferably, {B} is derived from a substituted or unsubstituted compound with acrylate or methacrylate groups or the thio analogs of these or the acid amides thereof. Very particularly preferably, {B} comprises one or more than one acrylate, methacrylate or thioacrylate group. Two, optionally even still more, different groups, e.g. an acrylate or one or two methacrylate groups or vice versa, can also be present in {B}. {B} can exhibit a continuous carbon backbone; however, the carbon chain(s) (main and/or side chain (s)) can also be interrupted by heteroatoms or groups, such as O, S, SO, NH, NHCO, PR, POR, CONHCO, COO, NHCOO or the like. The carbon backbone can be exclusively aliphatic and indeed with open and/or closed structures; however, {B} can also exhibit one or more aromatic nucleus or nuclei or condensed systems or triazine groups or the like, e.g. bisphenol A structures or the like. In addition, the groups or structures can be substituted in any way, e.g. with acid, acid amide, ester or amino groups. In comparison, the present invention is not to any great extent directed at compounds of the formula (I) in which {B} exhibits one or more isolated or oligomerized isoprene group(s) since these are generally relatively inert with regard to an additional organic crosslinking.

The residue {B} is connected via an ester, amide or thioester bridge —C(O)X— to the part of the molecule ($R^1$) ($R^2$)P(O)—($CHR^3$)—($CHR^4$)—($CHR^5$)$_m$ which exhibits the phosphorus-comprising group.

It is preferable for X to represent oxygen or nitrogen. Particularly preferably, X is oxygen.

In addition, it is particularly preferable for the residue {B} to comprise at least one acrylate group, methacrylate group or glycidyl group and especially for it to comprise more than one such group. The acrylate and/or methacrylate groups can be esterified with a relatively short-chain oligoalcohol (in particular an oligoalcohol comprising three to ten carbon atoms), e.g. a di- or tri- or tetra- or pentaalcohol, such as glycol, glycerol, trimethylolpropane or pentaerythritol or the like, the alcohol preferably being bonded via another of its alcohol functional groups to the C(O)X group. Instead of the alcohol functional groups, it is also possible in suitable cases for thio or amine functional groups to be present; optionally also mixed with alcohol functional groups. Then either the coupling group CO(X) can be an acid amide group or thioester group and/or the above-mentioned groups comprising a double bond can be bonded via amine or thio functional groups. In these cases, {B} comprises, e.g., thio(meth)acrylate or (meth)acrylamide groups. {B} can comprise the oligo (meth)acrylic esters, oligo(meth)acrylamides or oligo(meth) acrylic thioesters outlined above or, however, also consist thereof. In this group, the oligo(meth)acrylic esters are preferred.

In particularly preferred embodiments of the invention, a combination of at least two of the groups or indices mentioned in the above paragraphs as preferred or particularly preferred is realized, in highly preferred embodiments at least three and in more highly preferred at least four. Very particularly preferably, in the last case, the residue {B} has one, two, three or even more residues chosen from acrylate residues or methacrylate residues or a mixture of the two.

Additional embodiments of the invention arise from the enclosed subclaims.

(Meth)acryloyloxyalkoxysilanes functionalized with a carboxylic acid which are distinguished by a great variety of possibilities of varying or adjusting the properties of the inorganic/organic composite polymers resulting therefrom are disclosed in DE 44 16 857 A1. Additional reaction possibilities (e.g. glass ionomer reactions) and improved adhesion to inorganic surfaces arise partially through the carboxylic acid groups present. However, the phosphorus compounds now revealed far surpass the coupling action of the carboxylic acid residues present in the compositions mentioned there. For this reason, materials are prepared with the present compounds of the formula (I) which are superior to the substances proposed therein.

The compounds according to the invention can be prepared in different ways. They are successfully prepared, particularly favorably and conveniently, in addition based on cheap starting compounds, by the reaction of compounds of the formula (II)

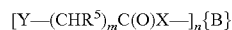

$$[Y-(CHR^5)_m C(O)X-]_n\{B\} \qquad II$$

with corresponding phosphorus compounds which comprise a P—H bond, e.g. dialkyl phosphites HP(O)(OR)$_2$, dialkylphosphine oxides HP(O)R$_2$ or mixed compounds (e.g. $R^1$ alkyl, $R^2$ alkoxy). The reaction is preferably carried out with addition of a radical (e.g. with nonactivated double bonds) or basic (e.g. with activated double bonds) catalyst, e.g. a sodium alkoxide or a tertiary amine, e.g. a trialkylamine compound. In this connection, Y is an organic group, e.g. a vinyl, allyl, norbornene or glycidyl group, which reacts in this reaction with the hydrogen bonded to the phosphorus atom to give a ($CHR^3$)—($CHR^4$) group. Preferably, Y is a group which is part of a Michael system, e.g. the CH$_2$=CZ residue with Z equal to H or CH$_3$, and simultaneously m is in this embodiment preferably 0, i.e. Y—C(O) is in this case a (meth) acrylate residue (if X is equal to O) or a corresponding derivative (e.g. with X equal to S or NR$^6$ with R$^6$ equal to hydrogen, $C_1$-$C_6$-alkyl or $C_6$-$C_{12}$-aryl). Very suitable is the reaction of dialkyl phosphites with oligo(meth)acrylates, such as trimethylolpropane trimethacrylate (TMPT(M)A) or pentaerythritol triacrylate or (meth)acrylates of the following formulae:

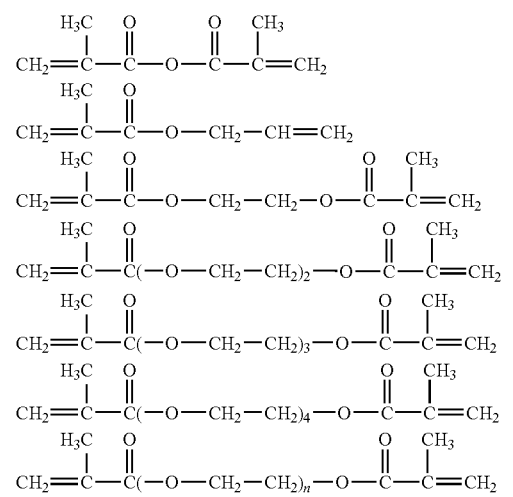

n = 9

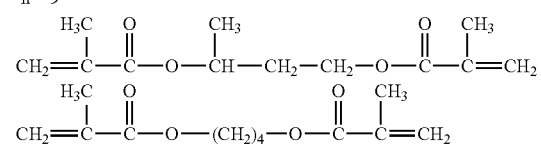

-continued
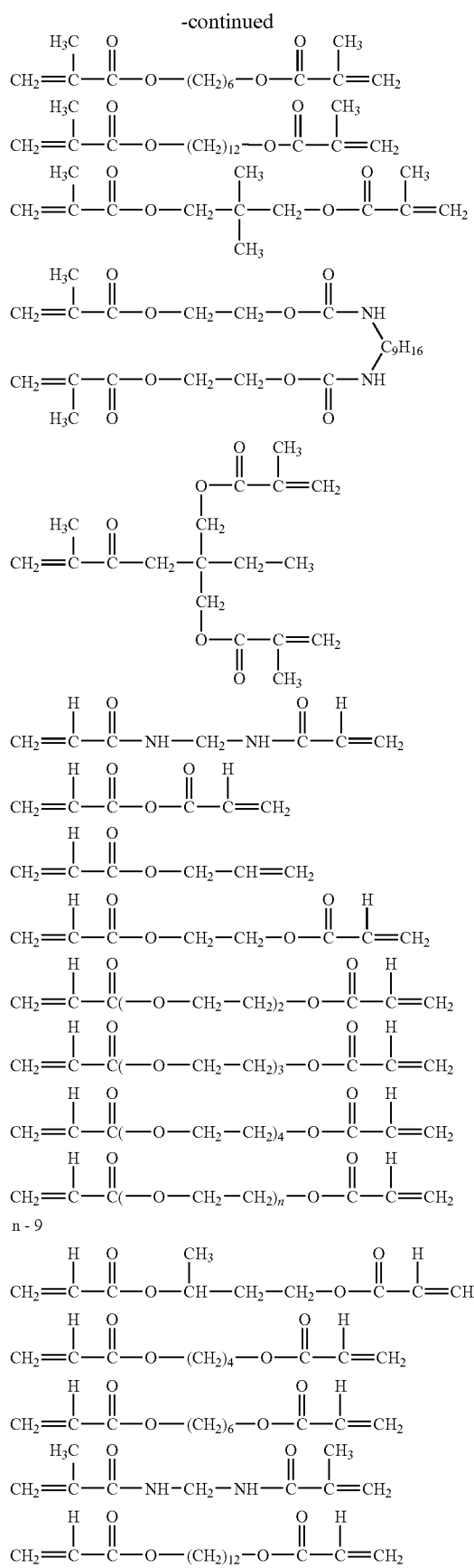
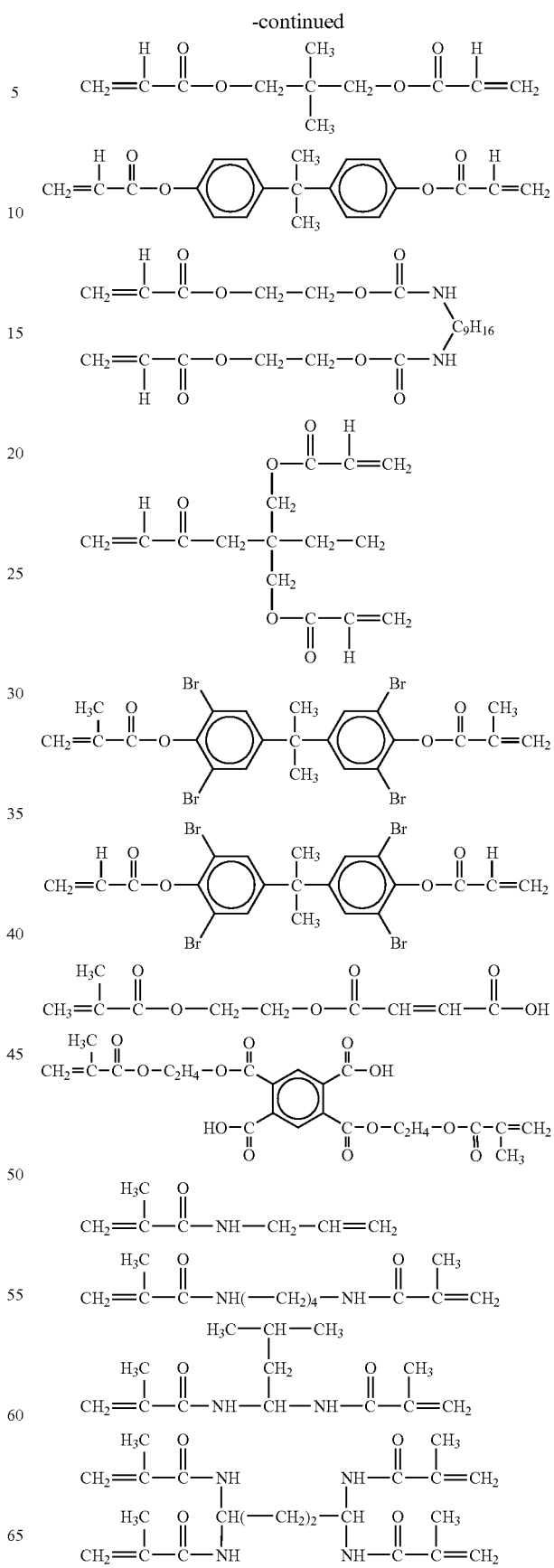

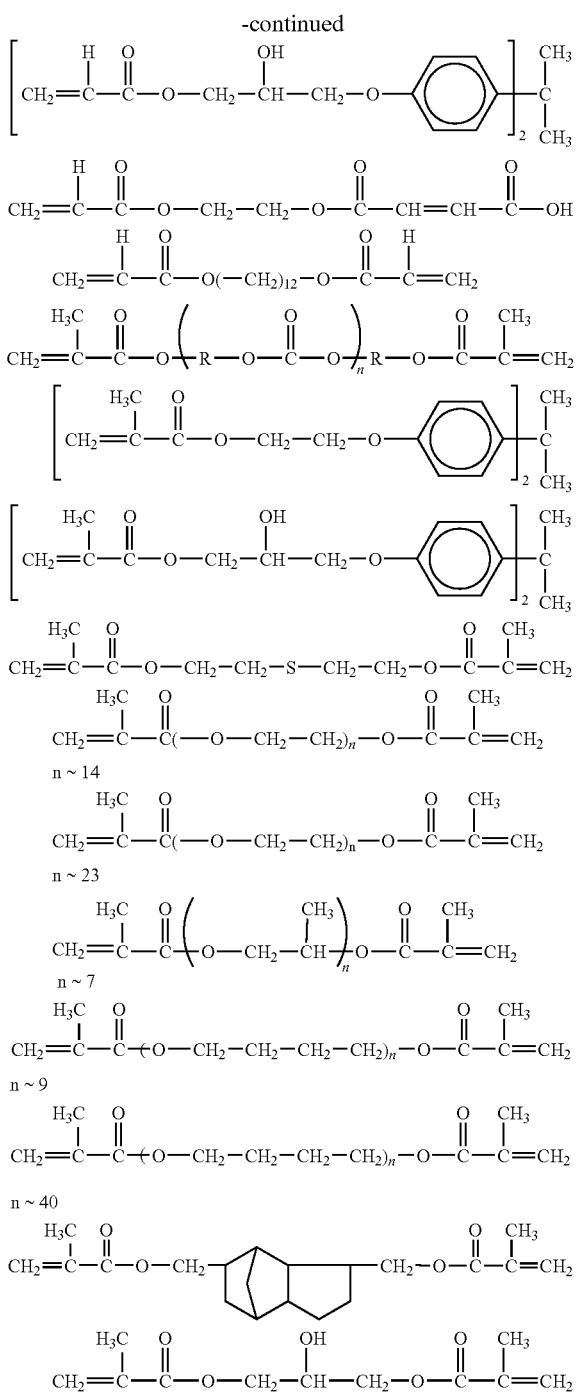

If in cases, in which n is greater than 1 in the formula (II), the phosphorus compound is not added in an equivalent amount but in a deficiency, for example with 1.5 mol per mole of a compound of the formula (II) with n equal to 2, mixtures of compounds of the formula (I) are thus obtained. A constituent of this mixture will then generally be a compound of the formula (I) in which n is equal to 2 and an additional constituent a compound of the formula (I) in which n is equal to 1 and in which {B} comprises an additional group [Y—(CHR$^5$)$_m$C(O)X—] which, for example, can be esterified with an alcohol functional group of {B}.

The alkoxy groups bonded to the phosphorus can subsequently as required be converted to hydroxyl groups in a simple way by measures known to a person skilled in the art (e.g. by hydrolysis).

The compounds according to the invention can either be polymerized as such via their organically polymerizable groups or can be incorporated (polymerized, subjected to polyaddition) in other polymers via these groups. Thus, they can, for example, act as constituents of purely organic copolymers or, in a particularly advantageous way, can be organically polymerized together with materials intended for Ormocers® (hydrolytically condensable substances or already hydrolytically condensed sols/gels) (Ormocers® are inorganic-organic polymer materials which can be obtained by hydrolysis of hydrolyzable silanes and optionally hydrolyzable compounds of other metals, as well as optionally an organic crosslinking of organic constituents of the abovementioned silanes and/or of additional components). The purely organic or inorganic-organic polymers (homopolymers or hybrid materials) obtained in this way can, for example, be used in the form of bulk materials, composites, cements, adhesives, filling compounds, coating compounds, bonding agents or as binders for ceramic particles (in ceramic molding processes). In addition, they are suitable, for example, for the preparation or priming of fillers and fibers, for abrasive wheels or for use in reactive extruders or the like. In this connection, their organically polymerizable group(s) can be crosslinked photochemically, thermally or under the effect of radiation or can be incorporated in the organic network of the cocomponents. An example of possible incorporation reactions is the thiol-ene addition, in which the compounds according to the invention can be added to thiols. Alternatively, self-curing processes are possible, for example a covalent-nucleophilic process (e.g. by amino curing) or via redox reactions, which can optionally be combined with photoinduced or thermal curing.

The compounds according to the invention have advantageous properties or property combinations and these properties or property combinations should also be inherent in the products which can be prepared therefrom or therewith (homopolymers or hybrid materials). These properties are very strongly dependent on the type of the $R^1$ and $R^2$ groups. The nature of these groups essentially determines the acidity, the conductivity, the polarity, the reactivity and the complexing capacity. Acidity, conductivity, polarity and reactivity, in particular also the corrosive capacity and also the complexing capacity, decrease in the order $R^1/R^2$ equal to OH/OH, OH/OR, OH/R, OR/OR, R/OR, R/R (with R here in the meaning alkyl, alkenyl, aryl, alkylaryl or arylalkyl). Compounds with $R^1/R^2$ equal to R/OR or R/R can accordingly then be used if less aggressive compounds are necessary and milder surfaces are to be produced. The following may be mentioned by way of example: the fact that the phosphorus-comprising group can be a charge carrier (namely for $R^1$ and/or $R^2$=hydroxyl or alkoxy, aryloxy, and the like, which can be converted to hydroxyl) makes possible the preparation of aqueous emulsions or dispersions from or with the compounds according to the invention or (pre)polymers thereof which have advantageous properties with regard to their conductivity, are suitable, for example, for electrodipping and are or can be antistatic. The phosphorus-comprising group can be catalytically effective, for which reason it can, for, example, serve as acidic copolymerizable catalyst, e.g. for the hydrolytic condensation in the sol-gel process for the preparation of (hetero)polycondensates, e.g. with Si—O—Si bridges. The presence or addition of the compounds according to the invention allows in this connection, since they can be incorporated via their organically polymerizable part with other organically polymerizable groups in the polycondensate in the network of the final product, a later separation stage of the catalyst otherwise to be employed to be dropped. Because of the polarity of the phosphorus-comprising group, the compounds according to the invention are furthermore very soluble in polar media. The phosphorus-comprising group in addition provides good properties of adhesion to inorganic, organic and hybrid (inorganic-organic) surfaces and more especially as well then if $R^1$ and/or $R^2$ represent hydroxyl. Their ability to complex/bind titanium, zirconium, tin, calcium and other metal and transition metal ions makes it possible to expect a modification in or adjustment to properties, such as the x-ray opacity, the refractive index and the contact toxicity, of the materials prepared from the compounds according to the invention. In addition, the phosphorus-comprising groups have an antimicrobial effect and they can, above all though with residues $R^1$ and/or $R^2$ equal to hydroxyl, be used as reactive groups in cement formation reactions or for the growth of inorganic materials, e.g. hydroxyapatite, which makes them appear suitable for the medical field, in particular the dental field. Chemically, the phosphorus-comprising groups can be additionally functionalized and, physically, the products prepared with the compounds according to the invention have a high temperature stability, good corrosion protection and flame resistance (internal matrix flame retardant), the flame-retardant effect increasing with the number of the phosphorus atoms in the material.

Compounds of the present invention according to formula (I) in which at least one, preferably both, of the groups $R^1$ and $R^2$ represents OR or hydroxyl are particularly suitable for the medical sector, in particular the dental field. The reason lies in the above-mentioned properties of these compounds. In particular, the substances prepared therefrom or therewith have uses as bonding agent, as matrix constituent for cements, for the growth of natural tooth or bone tissue, as composites, compomers, filling compounds or adhesives. In addition, for the above-mentioned purposes of substances for use in the dental field, those compounds are particularly suitable which, instead of or in addition to the above-mentioned features, comprise several double bonds, above all several double bonds incorporated in a Michael system, since these make possible closer-meshed organic crosslinking. It is also possible to use for this, in a suitable way, mixtures of compounds according to the invention which, e.g., as explained above, can be obtained by reacting a compound of the formula (II) with n greater than 1 with a deficiency of phosphorus compound with reference to the reactive groups Y. The mixture obtained then comprises a compound with an additional group [Y—(CHR$^5$)$_m$C(O)X—].

The invention is subsequently to be more fully explained on the basis of examples.

Reaction Scheme:

(Reaction of an Oligo(meth)acrylate with a Phosphite and Subsequent Hydrolysis)

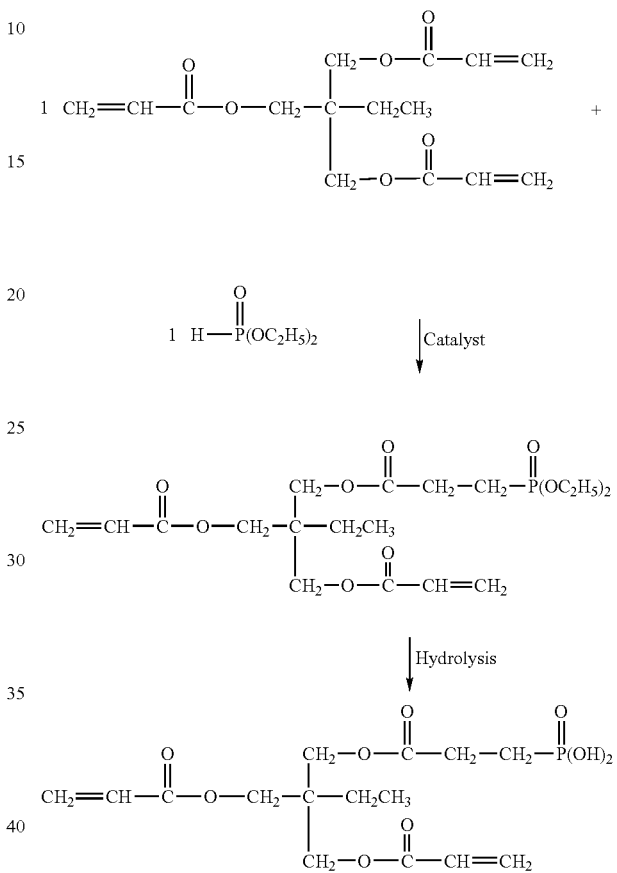

EXAMPLE 1

Reaction of Trimethylolpropane Triacrylate (TMPTA) with Diethyl Phosphite

First 2.13 g of diethyl phosphite (15.5 mmol) and subsequently a 25% sodium methoxide solution as catalyst are added to 4.61 g (15.5 mmol) of TMPTA in a flask under a dry protective gas atmosphere with cooling (exothermic reaction!) and with stirring. A fast reaction occurs which is complete within a few minutes. The course of the reaction and consequently the complete conversion of this exothermic PH addition can be established by means of IR spectroscopy from the following changes:

disappearance of the $v_{PH}$ band at 2426 cm$^{-1}$, decrease in the $v_{CH}$ band (olefin) at ca. 3040 cm$^{-1}$, decrease in the $v_{C=C}$ band at 1635/1619 cm$^{-1}$, emergence of the $v_{C=O}$ ester band at 1739 cm$^{-1}$ and accordingly overlapping of the $v_{C=O}$ acrylate band at 1728 cm$^{-1}$, which decreases.

The resulting phosphonate-modified acrylate (isomer mixture) can be isolated by the usual workup or, preferably, can be directly reacted further.

EXAMPLE 2

Reaction of Trimethylolpropane Trimethacrylate (TMPTMA) with Diethyl Phosphite

First 10.8 g of diethyl phosphite (76.5 mmol) and subsequently a 25% sodium methoxide solution as catalyst are added to 25.9 g (76.5 mmol) of TMPTMA in a flask under a dry protective gas atmosphere with cooling (exothermic reaction!) and with stirring. A fast reaction occurs which is complete within a few minutes. The course of the reaction and consequently the complete conversion of this exothermic PH addition can be established by means of IR spectroscopy from the following changes:

disappearance of the $\nu_{PH}$ band at 2426 cm$^{-1}$,
decrease in the $\nu_{CH}$ band (olefin) at ca. 3040 cm$^{-1}$,
decrease in the $\nu_{C=C}$ band at 1638 cm$^{-1}$,
emergence of the $\nu_{C=O}$ ester band at 1738 cm$^{-1}$ and accordingly overlapping of the $\nu_{C=O}$ methacrylate band at 1721 cm$^{-1}$, which decreases.

The resulting phosphonate-modified methacrylate (isomer mixture) can be isolated by the usual workup or, preferably, can be directly reacted further.

EXAMPLE 3

Reaction of Glycerol Dimethacrylate with Diethyl Phosphite

First 10.05 g of diethyl phosphite (72.4 mmol) and subsequently a 25% sodium methoxide solution as catalyst are added to 16.4 g (72.4 mmol) of glycerol dimethacrylate in a flask under a dry protective gas atmosphere with cooling (exothermic reaction!) and with stirring. A fast reaction occurs which is complete within a few minutes. The course of the reaction and consequently the complete conversion of this exothermic PH addition can be established by means of IR spectroscopy from the following changes:

disappearance of the $\nu_{PH}$ band at 2426 cm$^{-1}$,
decrease in the $\nu_{C=C}$ band at 1638 cm$^{-1}$,
emergence of the $\nu_{C=O}$ ester band at 1738 cm$^{-1}$ and accordingly overlapping of the $\nu_{C=O}$ methacrylate band at 1721 cm$^{-1}$, which decreases.

The resulting phosphonate-modified methacrylate (isomer mixture) can be isolated by the usual workup or, preferably, can be directly reacted further.

EXAMPLE 4

Reaction of Glycerol Acrylate Dimethacrylate with Diethyl Phosphite

A basic catalyst is slowly added dropwise to a mixture of 32 g (0.1133 mol) of glycerol acrylate dimethacrylate and 15.65 g (0.1133 mol) of diethyl phosphite under a dry protective gas atmosphere and with stirring. A fast reaction occurs with complete conversion of the diethyl phosphite, visible in the disappearance of the $\nu_{PH}$ band at 2426 cm$^{-1}$. The resulting liquid phosphonate comprising double bonds can be isolated by the usual workup. That the synthesis of the phosphonate compound has been carried out successfully can be established with the help of $^1$H NMR, $^{13}$C NMR and FTIR spectroscopy. The following NMR data are obtained for the acrylate-added phosphonate:

$^1$H NMR (400 MHz, CDCl$_3$, δ [ppm]): 1.32 (t, 6H, P(OCH$_2$CH$_3$—)$_2$), 1.94 (s, 6H, 2×=CCH$_3$—), 2.06 (m, 2H, PCH$_2$CH$_2$—), 2.62 (m, 2H, PCH$_2$CH$_2$—), 4.0-4.6 (m, 8H, P(OCH$_2$CH$_3$)$_2$, —OCH$_2$CH(O—)CH$_2$O—), 5.38 (1H, —OCH$_2$CH(O—)CH$_2$O—), 5.61 and 6.11 (s, 4H, 2×CH$_2$=)

$^{13}$C NMR (100 MHz, CDCl$_3$, δ [ppm]): 16.70 (POCH$_2$CH$_3$), 18.25 (=CHCH$_3$—), 20.23 and 21.67 (PCH$_2$CH$_2$—), 27.54 (PCH$_2$CH$_2$—), 61.85 (POCH$_2$CH$_3$), 62.42 (—OCH$_2$CH(O—)CH$_2$—), 126.43 and 135.66 (C=CH$_2$), 166.72 (CH$_2$=C(CH$_3$)COO—), 174.76 (PCH$_2$CH$_2$COO—) IR (film):

$\nu_{PH}$ band at 2426 cm$^{-1}$ disappears in the reaction,
$\nu_{CH}$ band (olefin) at ca. 3040 cm$^{-1}$ decreases,
$\nu_{C=C}$ band at 1638 cm$^{-1}$ decreases,
emergence of the $\nu_{C=O}$ ester band at 1746 cm$^{-1}$ and accordingly overlapping of the $\nu_{C=O}$ methacrylate band at 1724 cm$^{-1}$, which decreases.

EXAMPLE 5

Hydrolysis of the Phosphonate Compound from Example 4

11.76 ml (0.0891 mol) of trimethylsilyl bromide are slowly added dropwise, at ambient temperature under a protective gas atmosphere and with stirring, to a solution of 15 g (0.0356 mol) of phosphonate compound (example 4) in 20 ml of anhydrous methylene chloride. The preparation is stirred at ambient temperature for 24 hours. The reaction mixture is subsequently concentrated, 15 ml of absolute methanol are added with stirring and the mixture is stirred at ambient temperature for 4 hours. The solvent is then stripped off under vacuum and the liquid product is obtained. The phosphonic acid and accordingly the completeness of the hydrolysis can be established with the help of $^1$H NMR, $^{13}$C NMR and FTIR spectroscopy.

$^1$H NMR (400 MHz, CDCl$_3$, δ [ppm]): 1.93 (s, 6H, 2×=CCH$_3$—), 2.09 (m, 2H, PCH$_2$CH$_2$—), 2.64 (m, 2H, PCH$_2$CH$_2$—), 4.0-4.60 (m, 4H, —OCH$_2$CH(O—)CH$_2$—), 5.38 (1H, —OCH$_2$CH(O—)CH$_2$O—), 5.61 and 6.11 (s, 4H, 2×CH$_2$=), 9.97 (s, POH)

$^{13}$C NMR (100 MHz, CDCl$_3$, δ [ppm]): 18.23 (=CHCH$_3$—), 20.81 and 22.27 (PCH$_2$CH$_2$—), 27.44 (PCH$_2$CH$_2$—), 62.44 (—OCH$_2$CH(O—)CH$_2$O—), 126.58 and 135.62 (C=CH$_2$), 166.86 (CH$_2$=C (CH$_3$)COO—), 171.55 (PCH$_2$CH$_2$COO—)

IR (film): $\nu_{C=C}$ bands at 1638 cm$^{-1}$; $\nu_{C=O}$ ester band at 1746 cm$^{-1}$; $\nu_{C=O}$ methacrylate band at 1724 cm$^{-1}$

EXAMPLE 6

Polymerization of the Phosphonic Acid from Example 5 for the Preparation of Molded Articles The phosphonic acid from example 5 with 1% of Lucirin TPO is introduced into a curing mold (e.g. 2×2×25 mm$^3$) The methacrylate groups are converted within the framework of a photoinduced radical polymerization, curing the resin.

EXAMPLE 7

Flame Test with Molded Articles from Example 6

After flame treatment (ca. 10 seconds long) of the molded articles from example 6 with a ca. 900° C. flame, an immediate self-extinguishing is observed after removal of the flame. On the other hand, a corresponding molded article without the phosphonic acid groups, i.e. on a purely organic basis, completely incinerates with a large flame.

EXAMPLE 8

Polymerization of the Phosphonic Acid from Example 5 for the Preparation of a Bonding Layer The phosphonic acid from example 5 with 1% of Lucirin TPO is, e.g., applied to dental tissue. The methacrylate groups are converted within the framework of a photoinduced radical polymerization, curing the resin (bonding agent for a dental composite).

EXAMPLE 9

Synthesis of Mono(Phosphinic Acid Ethyl Ester) Based on TMPTA

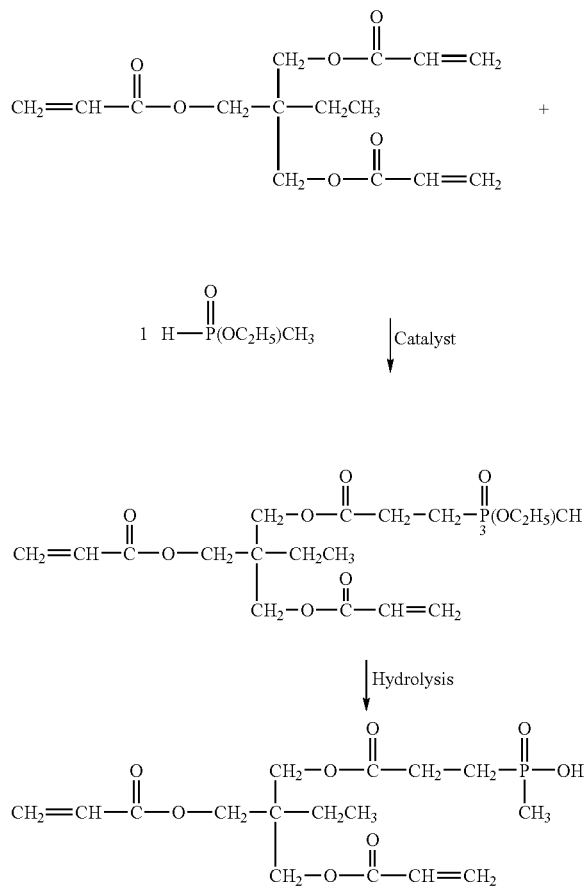

First 2.16 g of methylphosphinic acid ethyl ester (20.0 mmol) and subsequently a basic catalyst are added, under a dry protective gas atmosphere and with stirring, to 5.95 g (20.0 mmol) of trimethylolpropane triacrylate (TMPTA) in a flask. A fast reaction occurs with complete conversion of the phosphinic acid ester, visible in the disappearance of the $\nu_{PH}$ band. The course of the reaction and consequently the complete conversion of this PH addition can be established as usual (see example 1) using IR spectroscopy.

The resulting phosphonate-modified acrylate (isomer mixture) can be isolated by conventional workup and can be hydrolyzed using conventional methods (see, e.g., example 5).

What is claimed is:
1. A compound of the formula (I)

in which the substituents and indices have the following meanings:
X is NH, $NR^6$ or S,
$R^1$ and $R^2$ are, independently of one another, hydrogen or optionally substituted alkyl, alkenyl, aryl, alkylaryl or arylalkyl or optionally substituted alkoxy, aryloxy, alkylaryloxy, arylalkyloxy, or hydroxy;
$R^3$, $R^4$, $R^5$ and $R^6$ are, independently of one another, hydrogen or optionally substituted alkyl, alkenyl, aryl, alkylaryl, or arylalkyl,
{B} is a straight-chain or branched substituent with (i) more than one organically polymerizable group that contains a C=C moiety, and (ii) at least 4 carbon atoms, wherein at least one C=C moiety is bonded to the remaining part of {B} via an amine or thio functional group,
m is an integer from 0 to 20,
n is an integer from 1 to 20;
apart from compounds in which {B} exhibits one or more isolated or oligomerized isoprene groups.

2. The compound of the formula (I) as claimed in claim 1, wherein when $R^1$, $R^2$, $R^3$, $R^4$, $R^5$ or $R^6$ is an open chain aliphatic group, the aliphatic group contains 1-6 carbon atoms, and when $R^1$, $R^2$, $R^3$, $R^4$, $R^5$ or $R^6$ is a cycloaliphatic or aromatic group, the cycloaliphatic or aromatic group contains 6 to 12 carbon atoms.

3. The compound of the formula (I) as claimed in claim 1, wherein the substituents of the groups $R^1$, $R^2$, $R^3$, $R^4$, $R^5$ and $R^6$ are chosen from halogen, amino groups, oxygen-comprising substituents and/or sulfur-comprising substituents.

4. The compound of the formula (I) as claimed in claim 1, wherein $R^1$ and $R^2$ are both hydroxyl or wherein $R^1$ and $R^2$ are both optionally substituted alkoxy, aryloxy, alkylaryloxy or arylalkyloxy or wherein $R^1$ is optionally substituted alkoxy, aryloxy, alkylaryloxy or arylalkyloxy and $R^2$ is optionally substituted alkyl, alkenyl, aryl, alkylaryl or arylalkyl or wherein $R^1$ is OH and $R^2$ is optionally substituted alkyl, alkenyl, aryl, alkylaryl or arylalkyl or wherein $R^1$ and $R^2$ are both hydrogen or optionally substituted alkyl, alkenyl, aryl, alkylaryl or arylalkyl.

5. The compound of the formula (I) as claimed in claim 1, wherein X is NH or $NR^6$.

6. The compound of the formula (I) as claimed in claim 1, wherein m is 0, 1, 2, 3 or 4 and/or wherein n is 1, 2, 3 or 4.

7. The compound of the formula (I) as claimed in claim 6, wherein m is 0 and/or wherein n is 1.

8. The compound of the formula (I) as claimed in claim 1, wherein {B} exhibits up to 50 carbon atoms.

9. The compound of the formula (I) as claimed in claim 1, wherein {B} exhibits at least one thioacrylate or thiomethacrylate or (meth)acrylamide group.

10. The compound of the formula (I) as claimed in claim 9, wherein {B} further exhibits at least one vinyl, norbornene, glycidyl, acrylate, or methacrylate.

11. The compound of the formula (I) as claimed in claim 10, wherein the substituent {B} comprises at least one Michael systems selected from acrylate, methacrylate and/or glycidyl group(s).

12. The compound of the formula (I) as claimed in claim 11, wherein {B} comprises a carbon backbone derived from an oligoamine, one or more of the amino functional groups of the oligoamine being amidified with one or more acrylate and/or methacrylate groups.

13. The compound of the formula (I) as claimed in claim 9, wherein {B} comprises at least two thioacrylate or thiomethacrylate or (meth)acrylamide groups.

14. A process for the preparation of the compound of the formula (I) as defined in claim 1, comprising reacting compounds of the formula (II)

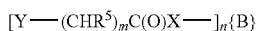

with compounds of the formula (III)

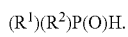

15. The process as claimed in claim 14, wherein the substituents $R^1$ and $R^2$ represent $C_1$-$C_6$-alkoxy.

16. The process as claimed in claim 15 for the preparation of compounds with the formula (I) in which the substituents $R^1$ and $R^2$ represent hydroxyl, further comprising, subjecting the product of the reaction of the compound with the formula (II) with the compound of the formula (III) to hydrolysis.

17. The process as claimed in claim 14, further comprising reacting 1 mol of the compound with the formula (II), wherein n is greater than 1, with less than n mol of the compound with the formula (III), n having the same meaning as in formula (II), in order to obtain a mixture with a compound of the formula (I), in which n is greater than 1, and a compound of the formula (II), in which n represents 1 and in which the group {B} comprises [Y—(CHR$^5$)$_m$C(O)X—].

18. A homopolymer of a compound of the formula (I)

in which the substituents and indices have the following meanings:

X is NH, NR$^6$ or S, $R^1$ and $R^2$ are, independently of one another, hydrogen or optionally substituted alkyl, alkenyl, aryl, alkylaryl or arylalkyl or optionally substituted alkoxy, aryloxy, alkylaryloxy, arylalkyloxy, or hydroxy, $R^3$, $R^4$, $R^5$ and $R^6$ are, independently of one another, hydrogen or optionally substituted alkyl, alkenyl, aryl, alkylaryl or arylalkyl, {B} is a straight-chain or branched substituent with (i) more than one organically polymerizable group that contains a C=C moiety, and (ii) at least 4 carbon atoms, wherein at least one C=C moiety is bonded to the remaining part of {B} via an amine or thio functional group, m is an integer from 0 to 20, n is an integer from 1 to 20;

apart from compounds in which {B} exhibits one or more isolated or oligomerized isoprene groups.

19. The homopolymer as claimed in claim 18, wherein the substituents $R^1$, $R^2$, $R^3$, $R^4$, $R^5$ and $R^6$ in each case comprise 1-6 carbon atoms for open-chain aliphatic groups and in each case comprise 6 to 12 carbon atoms for cycloaliphatic or aromatic groups.

20. A copolymer of different compounds of the formula (I)

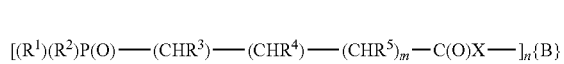

in which the substituents and indices have the following meanings:

X is NH, NR$^6$ or S, $R^1$ and $R^2$ are, independently of one another, hydrogen or optionally substituted alkyl, alkenyl, aryl, alkylaryl or arylalkyl or optionally substituted alkoxy, aryloxy, alkylaryloxy, arylalkyloxy, or hydroxy, $R^3$, $R^4$, $R^5$ and $R^6$ are, independently of one another, hydrogen or optionally substituted alkyl, alkenyl, aryl, alkylaryl or arylalkyl, {B} is a straight-chain or branched substituent with (i) more than one organically polymerizable group that contains a C=C moiety, and (ii) at least 2 carbon atoms, wherein at least one C=C moiety is bonded to the remaining part of {B} via an amine or thio functional group, m is an integer from 0 to 20, n is an integer from 1 to 20;

apart from compounds in which {B} exhibits one or more isolated or oligomerized isoprene groups.

21. The copolymer as claimed in claim 20, wherein when $R^1$, $R^2$, $R^3$, $R^4$, $R^5$ or $R^6$ is an open chain aliphatic group, the aliphatic group contains 1-6 carbon atoms, and when $R^1$, $R^2$, $R^3$, $R^4$, $R^5$ or $R^6$ is a cycloaliphatic or aromatic group, the cycloaliphatic or aromatic group contains 6 to 12 carbon atoms.

22. A copolymer formed by the use of monomer units of the formula (I) or of block polymer units constructed from monomers of the formula (I)

in which the substituents and indices have the following meanings:

X is NH, NR$^6$ or S, $R^1$ and $R^2$ are, independently of one another, hydrogen or optionally substituted alkyl, alkenyl, aryl, alkylaryl or arylalkyl or optionally substituted alkoxy, aryloxy, alkylaryloxy, arylalkyloxy, or hydroxy, $R^3$, $R^4$, $R^5$ and $R^6$ are, independently of one another, hydrogen or optionally substituted alkyl, alkenyl, aryl, alkylaryl or arylalkyl, {B} is a straight-chain or branched substituent with (i) more than one organically polymerizable group that contains a C═C moiety, and (ii) at least 4 carbon atoms, wherein at least one C═C moiety is bonded to the remaining part of {B} via an amine or thio functional group, m is an integer from 0 to 20,
n is an integer from 1 to 20;

apart from compounds in which {B} exhibits one or more isolated or oligomerized isoprene groups.

23. The copolymer as claimed in claim 22, wherein, when $R^1$, $R^2$, $R^3$, $R^4$, $R^5$ or $R^6$ is an open chain aliphatic group, then the aliphatic group contains 1-6 carbon atoms, and when $R^1$, $R^2$, $R^3$, $R^4$, $R^5$ or $R^6$ is a cycloaliphatic or aromatic group, the cycloaliphatic or aromatic group contains 6 to 12 carbon atoms.

* * * * *

UNITED STATES PATENT AND TRADEMARK OFFICE
CERTIFICATE OF CORRECTION

PATENT NO.         : 7,777,080 B2
APPLICATION NO.    : 10/527326
DATED              : August 17, 2010
INVENTOR(S)        : Herbert Wolter et al.

Page 1 of 4

It is certified that error appears in the above-identified patent and that said Letters Patent is hereby corrected as shown below:

Replace column 5, lines 12-19 with the following amended version of the fourth formula:

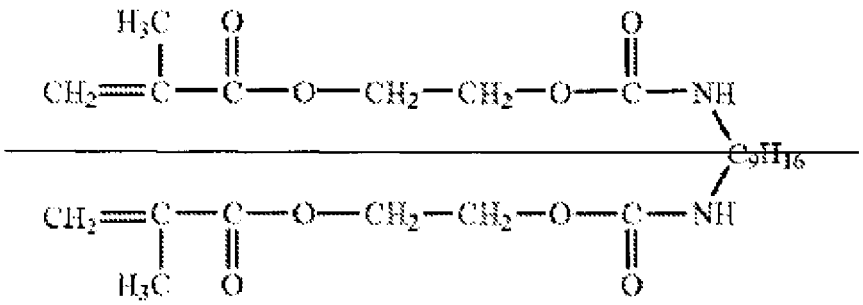

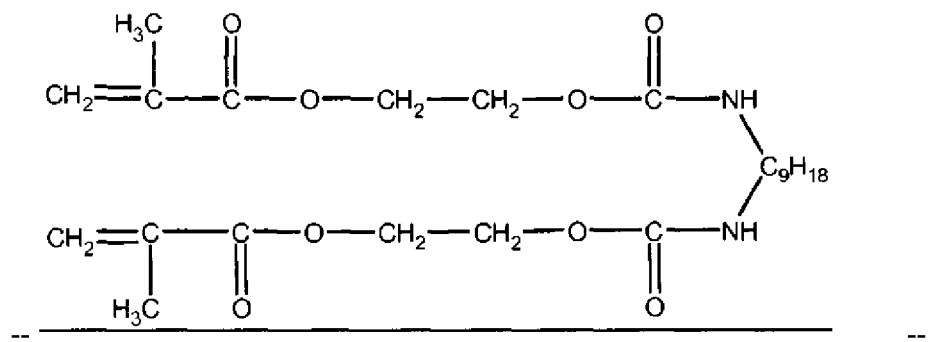

Signed and Sealed this
Twenty-ninth Day of November, 2011

David J. Kappos
*Director of the United States Patent and Trademark Office*

CERTIFICATE OF CORRECTION (continued)
U.S. Pat. No. 7,777,080 B2

Replace column 6, lines 12-18, with the following amended version of the third formula:

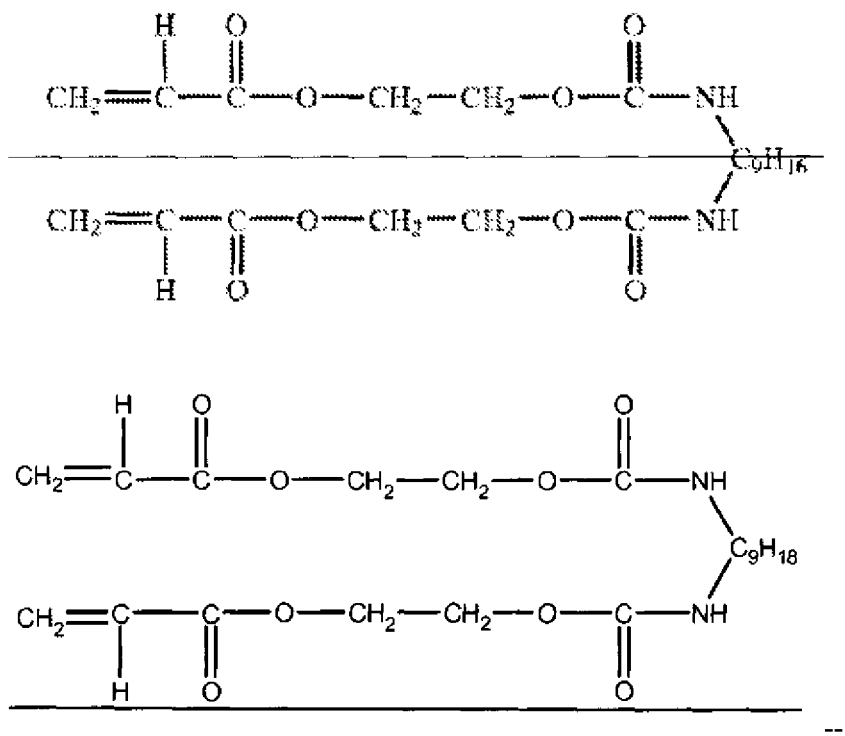

CERTIFICATE OF CORRECTION (continued)

Please replace column 6, lines 19-28 with the following amended version of the fourth formula:

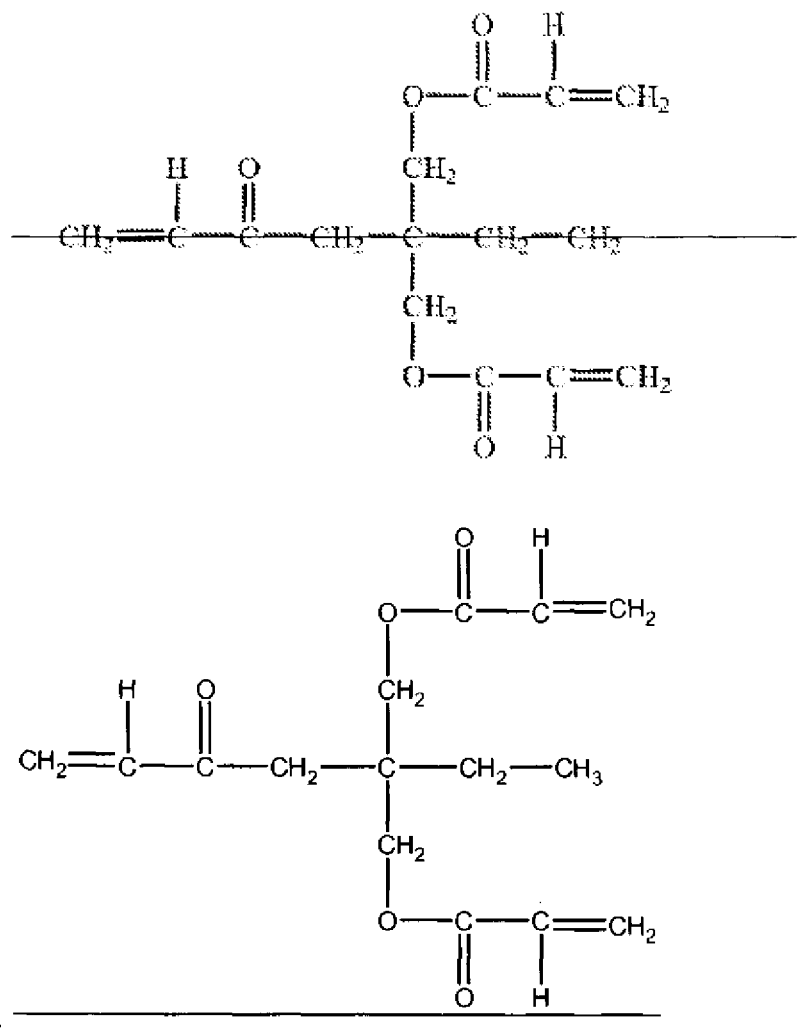

Replace column 6, lines 41-43 with the following amended version of the seventh formula:

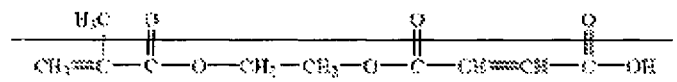

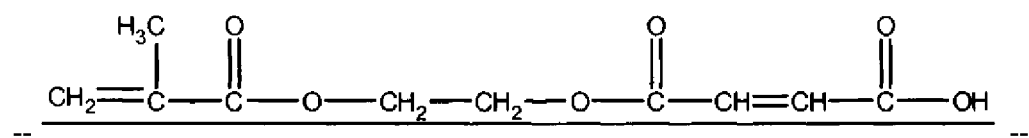

CERTIFICATE OF CORRECTION (continued)
U.S. Pat. No. 7,777,080 B2

Replace column 12, line 12 with the following amended version:

-- 62.42 (—OCH$_2$CH(O—)CH$_2$O—), 126.43 and 135.66 --

Replace column 12, line 42 with the following amended version:

-- PCH$_2$CH$_2$—), 4.0-4.60 (m, 4H, —OCH$_2$CH(O—)CH$_2$O—), --

Replace column 13, lines 41-47, with the following amended version of the third formula:

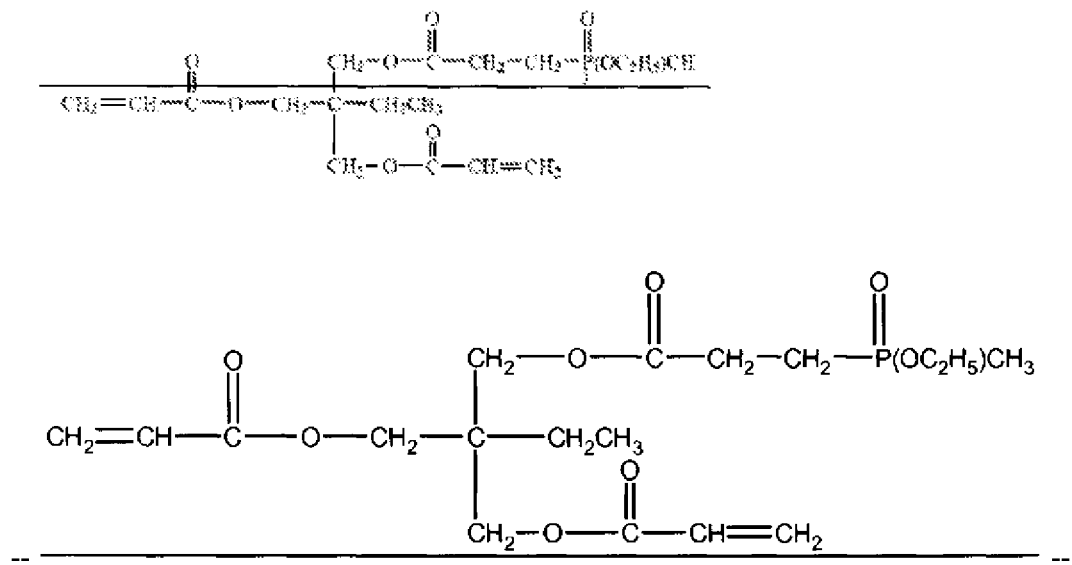

Replace column 14, line 67 with the following amended version:

-- glycidyl, acrylate, or methacrylate group. --